US010912739B2

(12) United States Patent
Frezza (10) Patent No.: US 10,912,739 B2
(45) Date of Patent: Feb. 9, 2021

(54) HYDROCOLLOID-BASED SKIN TREATMENT

(71) Applicant: PEACE OUT INC., San Francisco, CA (US)

(72) Inventor: Enrico Frezza, Stateline, NV (US)

(73) Assignee: PEACE OUT INC., San Francisco, CA (US)

(*) Notice: Subject to any disclaimer, the term of this patent is extended or adjusted under 35 U.S.C. 154(b) by 0 days.

(21) Appl. No.: 16/160,499

(22) Filed: Oct. 15, 2018

(65) Prior Publication Data

US 2019/0111005 A1    Apr. 18, 2019

Related U.S. Application Data

(60) Provisional application No. 62/572,643, filed on Oct. 16, 2017.

(51) Int. Cl.
| | |
|---|---|
| *A61K 9/70* | (2006.01) |
| *A61K 31/07* | (2006.01) |
| *A61K 31/555* | (2006.01) |
| *A61K 9/00* | (2006.01) |
| *A61K 31/133* | (2006.01) |
| *A61K 47/38* | (2006.01) |
| *A61K 8/04* | (2006.01) |
| *A61L 15/44* | (2006.01) |
| *A61Q 19/00* | (2006.01) |
| *A61L 15/60* | (2006.01) |
| *A61K 8/67* | (2006.01) |
| *A61K 8/49* | (2006.01) |
| *A61K 8/27* | (2006.01) |
| *A61L 15/46* | (2006.01) |
| *A61K 8/02* | (2006.01) |
| *A61Q 19/10* | (2006.01) |

(52) U.S. Cl.
CPC .......... *A61K 9/7007* (2013.01); *A61K 8/0208* (2013.01); *A61K 8/044* (2013.01); *A61K 8/27* (2013.01); *A61K 8/4913* (2013.01); *A61K 8/671* (2013.01); *A61K 9/0043* (2013.01); *A61K 31/07* (2013.01); *A61K 31/133* (2013.01); *A61K 31/555* (2013.01); *A61K 47/38* (2013.01); *A61L 15/44* (2013.01); *A61L 15/46* (2013.01); *A61L 15/60* (2013.01); *A61Q 19/00* (2013.01); *A61Q 19/008* (2013.01); *A61K 9/0014* (2013.01); *A61Q 19/005* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 4,538,603 A * | 9/1985 | Pawelchak | A61L 15/18 424/447 |
| 5,569,207 A | 10/1996 | Gisselberg et al. | |
| 5,585,109 A | 12/1996 | Hayward et al. | |
| 5,885,237 A | 3/1999 | Kadash et al. | |
| 6,471,986 B1 | 10/2002 | Cline et al. | |
| 7,470,437 B2 * | 12/2008 | Burrell | A61K 9/0014 424/618 |
| 8,858,988 B2 | 10/2014 | Chamberland et al. | |
| 2002/0147265 A1 | 10/2002 | Ding et al. | |
| 2005/0080465 A1 | 4/2005 | Zelickson et al. | |
| 2005/0244525 A1 | 11/2005 | Callaghan et al. | |
| 2006/0253078 A1 | 11/2006 | Wu et al. | |
| 2009/0216169 A1 | 8/2009 | Hansen et al. | |
| 2010/0209515 A1 * | 8/2010 | Chantalat | A61Q 11/00 424/490 |
| 2014/0363488 A1 | 12/2014 | Hansen et al. | |
| 2017/0113038 A1 * | 4/2017 | Nagel | A61N 1/36034 |
| 2017/0304215 A1 | 10/2017 | Freeza | |
| 2018/0185196 A1 * | 7/2018 | Levinson | A61F 13/0246 |

FOREIGN PATENT DOCUMENTS

| | | |
|---|---|---|
| CN | 103143054 A | 6/2013 |
| CN | 204683911 U | 10/2015 |
| WO | 01/13968 A1 | 3/2001 |
| WO | 02/085387 A2 | 10/2002 |
| WO | 2014/159798 A1 | 10/2014 |

OTHER PUBLICATIONS

Agrawal, "Irreversible Hydrocolloid Alginate," Presentation Published Online at https:/1www.slideshare.net/amitshravgi/lginateirreversible-hyd rocolloid (Jan. 25, 2014).
Davies, P., "Comparison of foam and hydrocolloid dressings in the management of wounds: a review of the published literature," available at: http://www.worldwidewounds.com/2010/July/DaviesRippon/DaviesRippon.html, Apr. 2010, 1:tccessed Apr. 2, 2018.
"Hydrocolloid PSAs: New Formulation Strategies," MODI Medical Device and Diagnostic Industry News Products and Suppliers (Jun. 1, 1999) accessible at:(http://www.mddlonllne.com/article/hydrocolloid-psas-new-formulation-strategies).
Maver et al., "Functional wound dressing materials with highly tunable drug release properties," RCS Advances 5:77873-77884 (2015).
Swezey, L., "Hydrocolloid Dressings," available at https://woundeducators.com/hydrocolloid-dressings/, Aug. 26, 2010, accessed Jan. 10, 2018.
World Wide Wounds: Frequently Asked Questions: Hydrocolloid Dressings (Apr. 1998) accessible at: (http://www.Norldwidewounds.com/1998/april/Hydrocolloid-FAQ/hydrocolloid-questions.html).

* cited by examiner

*Primary Examiner* — Patricia Duffy
*Assistant Examiner* — Garen Gotfredson
(74) *Attorney, Agent, or Firm* — Frost Brown Todd LLC (57) ABSTRACT

The present technology relates generally to devices for treatment of skin and skin conditions, as well as methods for preparing the devices and methods of treatment using the devices. Suitably, the devices comprise a hydrocolloid dressing and one or more active agents, wherein the amount of the active agent(s) does not reduce the absorption properties of the hydrocolloid dressing.

9 Claims, 6 Drawing Sheets

HYDROCOLLOID FORMULATION NOTES:
Retinyl Acetate (Vitamin A) 0.5%
Topical Zinc Pyrrolidone 0.5%

| ITEM | DESCRIPTION | QTY. |
|---|---|---|
| 302 | CLEAR RELEASE LINER | 1 |
| 400 | 0.012" THICK EFTECH HYDROCOLLOID** W/ .0006" PU | 1 |

HYDROCOLLOID FORMULATION NOTES:
DMAE 0.5%
Retinyl Acetate (Vitamin A) 0.5%

| ITEM | DESCRIPTION | QTY. |
|---|---|---|
| 302 | CLEAR RELEASE LINER | 1 |
| 420 | 0.010" THICK EFTECH HYDROCOLLOID*** W/ .0006" PU | 1 |

FIG. 4C

HYDROCOLLOID-BASED SKIN TREATMENT

CROSS-REFERENCE TO RELATED APPLICATIONS

The present application claims benefit of U.S. Provisional Patent Application No. 62/572,643, filed Oct. 16, 2017, the disclosure of which is incorporated by reference herein in its entirety.

FIELD OF THE INVENTION

The present technology relates generally to devices for treatment of skin and skin conditions, as well as methods for preparing the devices and methods of treatment using the devices. Suitably, the devices comprise a hydrocolloid dressing and one or more active agents, wherein the amount of the active agent(s) does not reduce the absorption properties of the hydrocolloid dressing.

BACKGROUND OF THE INVENTION

Various skin conditions, including blackheads and clogged pores, are often treated using topically applied formulations. However, these formulations, while containing active ingredients, are often ineffective at being able to effectively remove and oil, dirt and bacteria that can lead to the skin conditions.

Another treatment methodology, generally known as "pore strips," contain ingredients that, when mixed with water, create a dense, glue-like adhesive. Polyquaternium-37, is an example of one such ingredient. The pore strip hardens as it dries on the surface of the skin, and the adhesive attaches to the top layer of dead skin cells, dirt, hair, oil and, blackheads (not to be confused with sebaceous filaments). While, pore strips are often able to "clean" the surface area of a patient's nose, in general, very little deep cleansing occurs, as often only the superficial portion of the blackhead is removed. While pore strips may successfully remove portions of the blackheads instantly at the time of application, there is no evidence that the strips treat blackheads from recurring on a consistent basis. In addition, pore strips can also cause skin irritation, and in cases of delicate or thin skin, can actually tear or damage the skin's surface.

What is needed is a device that can not only deliver effective active agents to the skin surface and underlying compromised areas, but also removes contaminants such as dirt, oil and bacteria, which are many times the cause of these underlying conditions, while not damaging the skin surface. The present application meets these needs.

BRIEF SUMMARY OF THE INVENTION

In view of the foregoing, provided herein are devices and methods for treating skin conditions which utilize the absorption properties of a hydrocolloid dressing in combination with one or more active agents.

In exemplary embodiments, provided herein are devices for treatment of skin, which suitably include a hydrocolloid dressing having a thickness of about 0.005 inches to about 0.015 inches, and active agents comprising vitamin A and zinc pyrrolidone associated with the hydrocolloid dressing. The active agents are present at an amount so as to not reduce the absorption capability of the hydrocolloid dressing.

In embodiments, the active agents are present at an amount of about 0.1% to about 10%. In certain embodiments, the vitamin A and the zinc pyrrolidone are each present at an amount of about 0.2% to about 0.7%, or are each present at an amount of about 0.5%.

Suitably, the hydrocolloid dressing has a thickness of about 0.010 inches to about 0.013 inches.

In additional embodiments, the active agents consist essentially of vitamin A and zinc pyrrolidone, each at about 0.5%.

In embodiments the hydrocolloid dressing is cut into a shape to fit over a bridge of a nose of a patient.

Also provided herein are devices for treatment of skin, which include a hydrocolloid dressing having a thickness of about 0.005 inches to about 0.012 inches, and active agents comprising vitamin A and dimethylethanolamine associated with the hydrocolloid dressing. As described herein, the active agents are suitably present at an amount so as to not reduce the absorption capability of the hydrocolloid dressing.

In embodiments, the active agents are present at an amount of about 0.1% to about 10%, for example, the vitamin A and the dimethylethanolamine are each present at an amount of about 0.2% to about 0.7%, including where the vitamin A and the dimethylethanolamine are each present at an amount of about 0.5%.

In embodiments, the hydrocolloid dressing has a thickness of about 0.008 inches to about 0.011 inches, and the active agents consist essentially of vitamin A and dimethylethanolamine, each at about 0.5%.

Also provided herein are methods of treating a skin condition, which include providing a device as described herein, wherein the active agents are present at an amount so as to not reduce the absorption capability of the hydrocolloid dressing, applying the device to a skin surface, and maintaining the device on the skin surface for a period of at least 1 hour, thereby treating the skin condition.

In embodiments, the device is maintained on the skin surface for a period of at least 6 hours, and suitably the method of treatment is repeated daily for a period of at least 3 days.

In embodiments, the skin condition is a blackhead, and suitably the device is applied to a bridge of a nose.

In additional embodiments, the skin condition is a clogged pore, and the device is applied to a check or chin skin surface.

In additional embodiments, the device further comprises a removable layer on an inner surface of the device, and the methods further comprise removing the removable layer prior to applying the device to the skin surface.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

DETAILED DESCRIPTION OF THE INVENTION

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present application pertains, unless otherwise defined. Reference is made herein to various methodologies and materials known to those of skill in the art.

Figure 1:
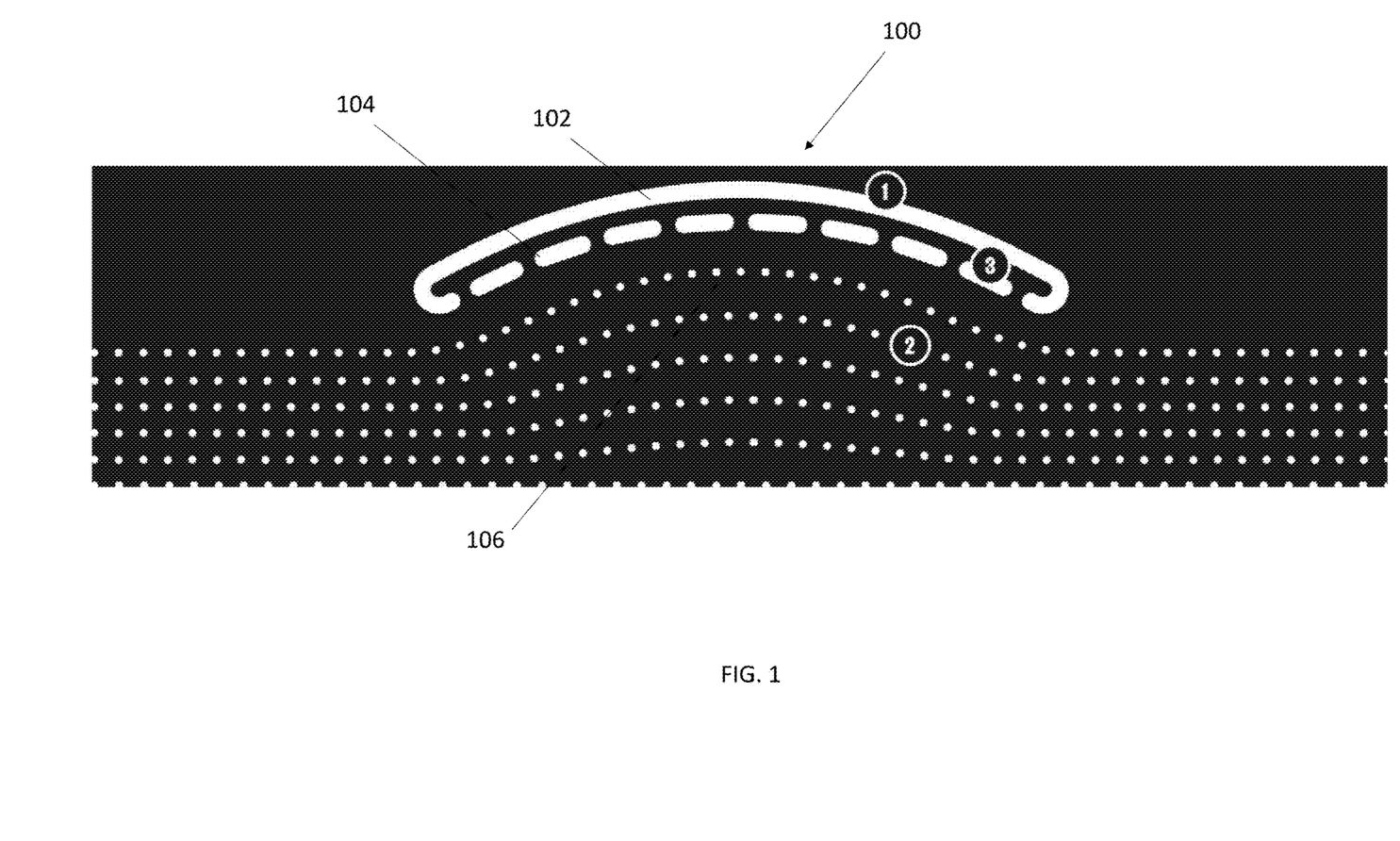
FIG. 1 shows a sectional view of a device for treatment of skin or skin conditions as described in embodiments herein.

In exemplary embodiments, as shown in FIG. 1, provided herein are devices 100 for treatment of skin 106 and skin conditions. In embodiments, device 100 suitably comprises a hydrocolloid dressing 102 and an active agent 104 (or combination of active agents) associated with the hydrocolloid dressing. In exemplary embodiments, the active agent(s) comprise vitamin A, zinc pyrrolidone and/or dimethylethanolamine (and various combinations thereof), associated with the hydrocolloid dressing.

The structure of device 100 in FIG. 1 is provided for illustrative purposes only and is not to be construed to provide the only structure or orientation for the device described herein.

As described herein, the active agent(s) is present at an amount so as to not reduce the absorption capability of the hydrocolloid dressing. It has been surprisingly discovered that by properly formulating the hydrocolloid dressing and active agent(s), the ability of the hydrocolloid dressing to absorb oil, pus, dirt, bacteria and other materials from the skin surface, and underlying skin conditions, is not reduced or impacted, i.e., the "absorption capability" of the hydrocolloid dressing is not reduced.

As used herein, a "hydrocolloid dressing" refers to a flexible sheet or wafer which contains material that forms a gel in the presence of water. Hydrocolloid dressings are suitably biodegradable, non-breathable, and can adhere to the skin without the use of adhesives or separate taping.

The active surface of a hydrocolloid dressing is coated with a cross-linked adhesive mass containing a dispersion of gelatin, pectin and carboxy-methylcellulose (e.g., sodium carboxymethylcellulose (NaCMC) together with other polymers and adhesives. Suitably the hydrocolloid is combined with elastomers and adhesives and applied to a carrier for example a polyurethane foam or film, to form an absorbent, self adhesive, waterproof wafer. In contact with a fluid (e.g., a wound exudate, pus, oil, blood, etc.), the polysaccharides and other polymers absorb water and swell, forming a gel which is held within the structure of the adhesive matrix. The gel which is formed as a result of the absorption of fluid is not mobile and free running but held within the structure of the adhesive matrix. Suitably, a hydrocolloid dressing is waterproof.

In suitable embodiments, hydrocolloid dressing is a hi-tack dressing, which can comprise a hydrophobic pressure sensitive adhesive (e.g., butyl rubber or a styrene-isoprene-styrene (SIS) block copolymer) compounded with hydrophilic particulates. As described herein, suitably the hydrocolloid dressing comprises a polyurethane carrier covering the non-contacting side of the dressing. In other embodiments, the hydrocolloid dressing can comprise cis-1,4-polyisoprene (Natural rubber) polybutadiene (butyl rubber) thermoplastic elastomer block copolymers, copolymers of alkyl acrylates. The hydrocolloid dressing suitably demonstrates a removable, high initial tack (i.e., high adhesion to a skin surface), which has a general-purpose removable adhesive with good internal strength, and stable adhesion. The dressings remove cleanly from most surfaces, including skin.

The devices described herein also aid in correcting any abnormal shedding of acne which helps to unclog pores and absorb the exudate of acne or blackheads.

In exemplary embodiments, the active agent is present in the devices at an amount of about 0.1% to about 10%. The percentage of active agent is measured as a weight/weight measurement based on the total weight of the hydrocolloid dressing. In embodiments, the devices comprise a single active agent, and in other embodiments, more than one (e.g., 2, 3, 4, 5, etc.,) active agents can be included in the devices described herein. In suitable embodiments, the active agents, if multiple active agents are utilized, are each present in an amount of about 0.1% to about 10%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1%, about 0.2% to about 0.7%, about 0.3% to about 0.6%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, or about 1.5%.

In exemplary embodiments, one of the active agents is vitamin A (retinyl acetate), suitably present at an amount of about 0.1% to about 10%, more suitably about 0.1% to about 1%, about 0.2% to about 0.7%, or about 0.2%, about 0.3%, about 0.4%, about 0.5%, about 0.6%, about 0.7%, about 0.8%, about 0.9%, or about 1%. Vitamin A (retinyl acetate) suitably acts as an exfoliating agent that encourages healthy cell turnover to minimize pore blockage and promote skin health.

In further embodiments, one of the active agents is zinc pyrrolidone, suitably present at an amount of about 0.1% to about 10%, more suitably about 0.1% to about 1%, about 0.2% to about 0.7%, or about 0.2%, about 0.3%, about 0.4%, about 0.5%, about 0.6%, about 0.7%, about 0.8%, about 0.9%, or about 1%. Zinc pyrrolidone is an antimicrobial agent that suitably acts to reduce excess bacteria and decrease inflammation on the skin.

In still further embodiments, one of the active agents is dimethylethanolamine, suitably present at an amount of about 0.1% to about 10%, more suitably about 0.1% to about 1%, about 0.2% to about 0.7%, or about 0.2%, about 0.3%, about 0.4%, about 0.5%, about 0.6%, about 0.7%, about 0.8%, about 0.9%, or about 1%. Dimethylethanolamine (DMAE) is an antioxidant that suitably acts to minimize pores, while smoothing and illuminating skin texture.

In additional embodiments, the active agents can comprise each vitamin A and zinc pyrrolidone, with each suitably present at an amount of about 0.1% to about 10%, more suitably about 0.1% to about 1%, about 0.2% to about 0.7%, or about 0.2%, about 0.3%, about 0.4%, about 0.5%, about 0.6%, about 0.7%, about 0.8%, about 0.9%, or about 1%.

In still further embodiments, the active agents can comprise each vitamin A and dimethylethanolamine, with each suitably present at an amount of about 0.1% to about 10%, more suitably about 0.1% to about 1%, about 0.2% to about 0.7%, or about 0.2%, about 0.3%, about 0.4%, about 0.5%, about 0.6%, about 0.7%, about 0.8%, about 0.9%, or about 1%.

Active agents can be associated with the hydrocolloid dressing in various ways known in the art, including for example, dispersed within the hydrocolloid dressing, coated on the hydrocolloid dressing, co-mixed with the components of the hydrocolloid dressing, or otherwise physically contacted with the hydrocolloid dressing so that the dressing and the active agent do not separate from one another until the dressing is applied to skin surface 106.

Figure 2A:
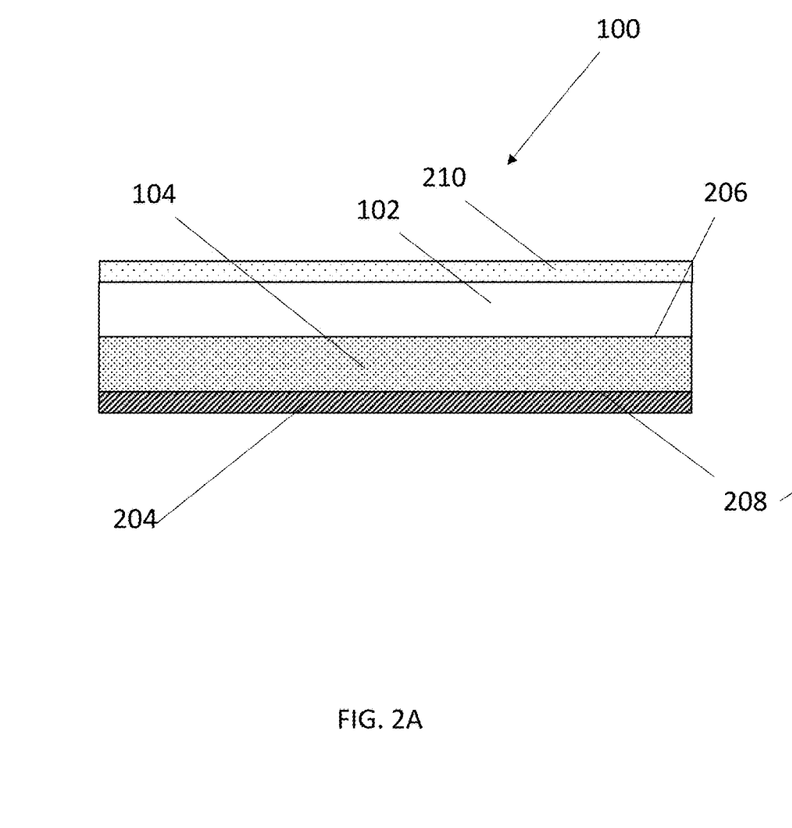
FIGS. 2A-2D show sectional views of further devices for treatment of skin or skin conditions as described in embodiments herein.
Figure 2B:
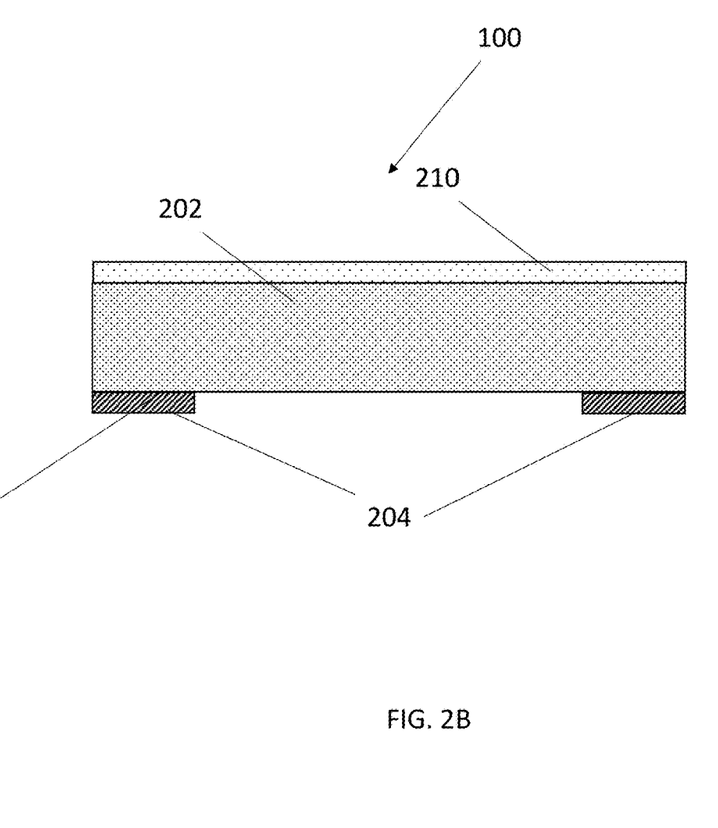

In embodiments, the active agent(s) is associated with an inner surface of the hydrocolloid dressing for contact with a skin surface (106 of FIG. 1). For example, as shown in FIG. 2A, active agent 104 can be coated on an inner surface 206 of hydrocolloid dressing 102, or loaded into the hydrocolloid dressing so as to be more concentrated at the inner surface 206. In other embodiments, active agent(s) is dispersed throughout the hydrocolloid dressing in a uniform or fairly uninform manner (see 202 of FIG. 2B), so as to readily diffuse from the hydrocolloid dressing to the skin surface. Hydrocolloid dressing 102 also suitably further comprises carrier 210, which suitably is a polyurethane foam or film. Carrier 210 helps provide stability to the hydrocolloid dressing, and also protect the surface of the dressing away from the skin surface (i.e., the non-contact surface) from dirt or other contaminants. The terms "carrier" and "laminate" are used interchangeably herein.

Figures 2C, 2D:
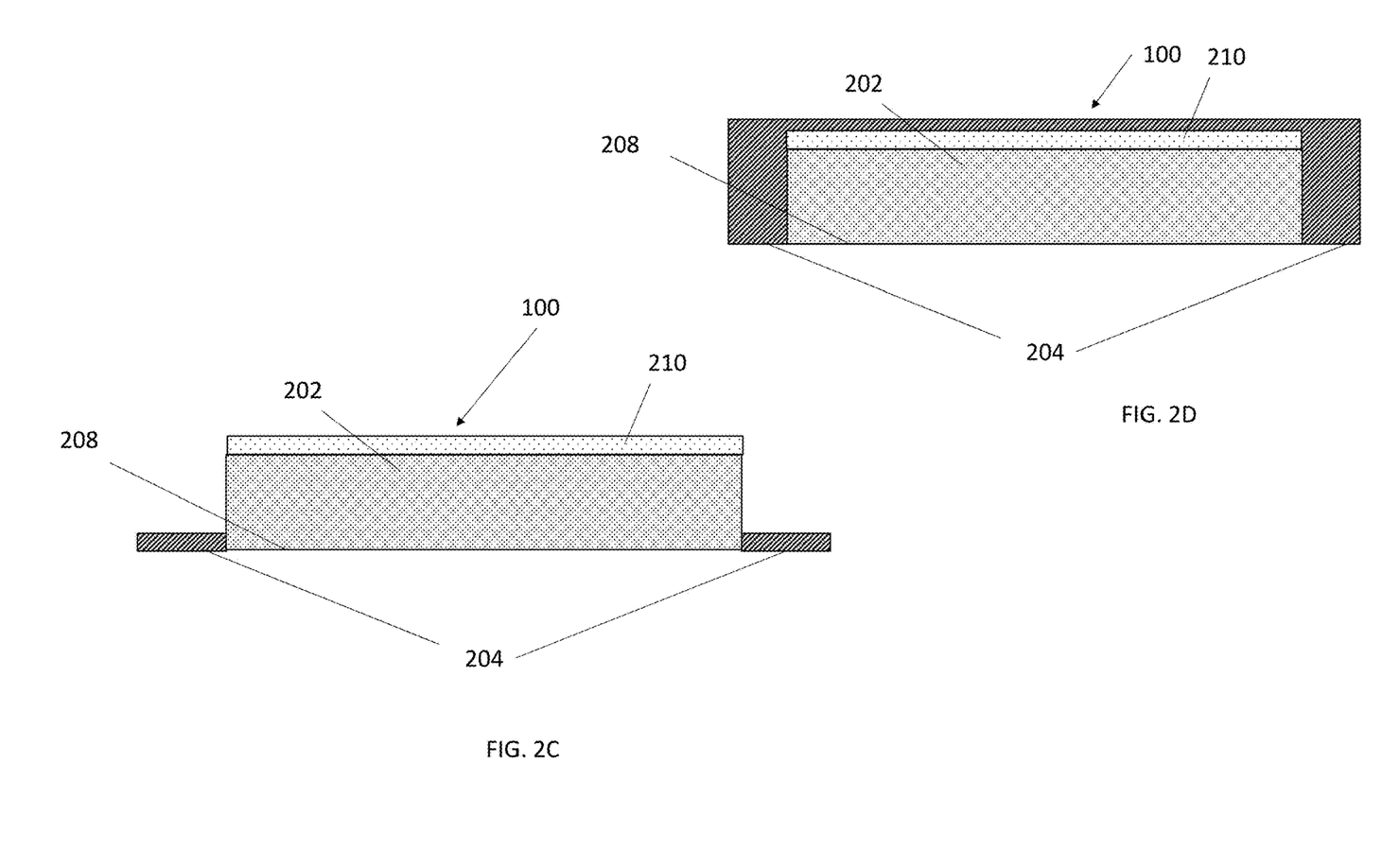

As described herein, the devices comprising the hydrocolloid dressings suitably adhere to the skin surface without any further need for an adhesive or tape. However, in additional embodiments, the inner surface of the devices 208 can further comprise an adhesive 204 for adhering to the skin surface. Adhesive 204 can fully cover the active agent-associated hydrocolloid dressing (FIG. 2A), or can simply be present at the external edges of the hydrocolloid dressing (FIG. 2B), or completely external to the inner surface of the devices 208 (FIG. 2C or FIG. 2D), so as to not interfere with the diffusion of the active agent, and the absorption of oil, pus, etc., from the skin surface.

Figure 3A:
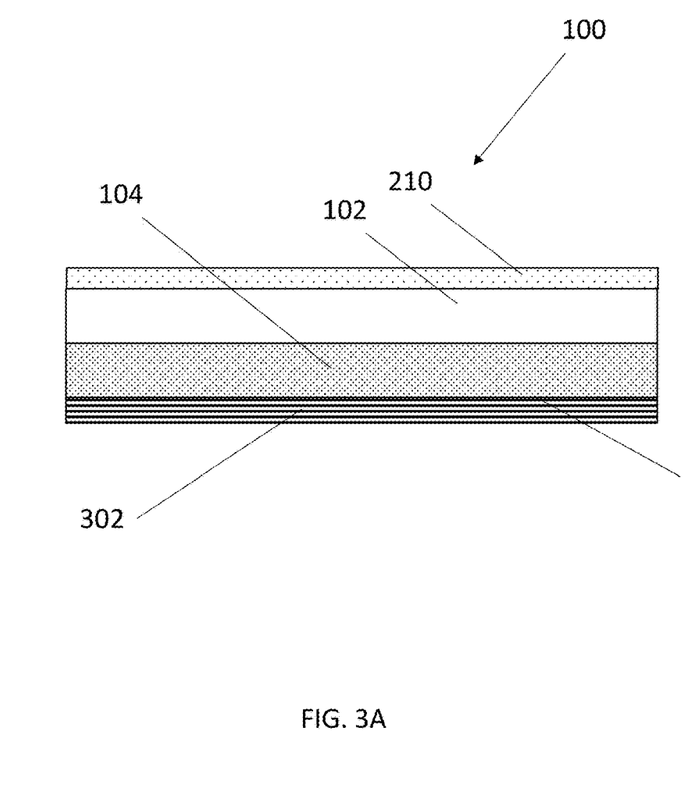
FIGS. 3A-3B show sectional views of still further devices for treatment of skin or skin conditions as described in embodiments herein.
Figure 3B:
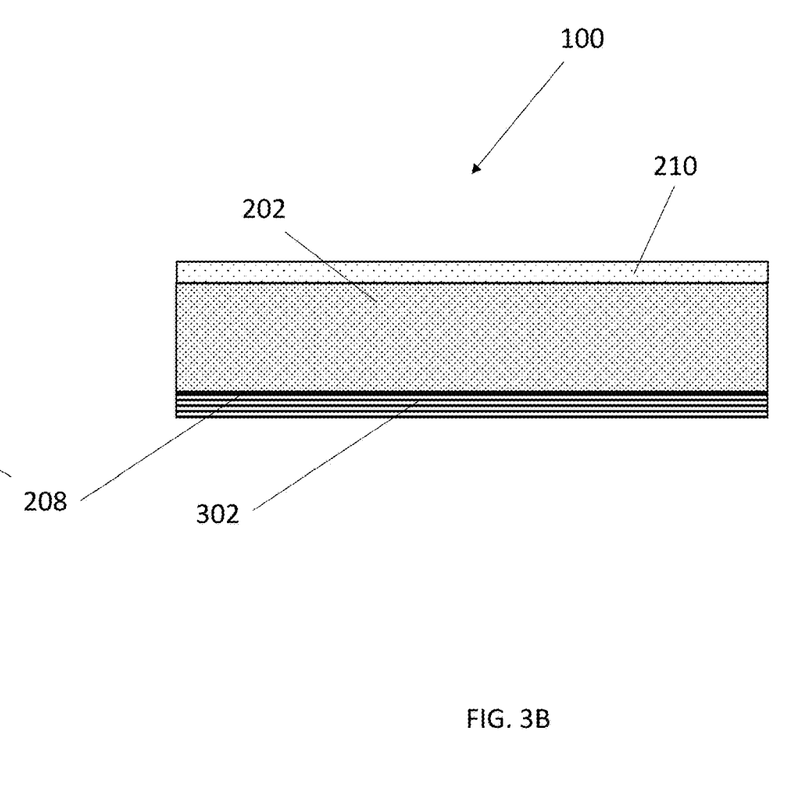

In further embodiments, as shown in FIGS. 3A-3B, the devices described herein 100 can further comprise a removable layer 302 covering the inner surface of the devices 208. The terms "removable layer," "removable liner" and "liner" are used interchangeably herein. This removable layer acts as a barrier to dirt and bacteria contacting the device, and also a way to maintain the cleanliness, including sterility, of the devices prior to use on a skin surface. The layer also acts to prevent the devices 100 from sticking to a skin surface prior to a desired use. Removable layer 302 can be a thin layer of paper, cloth, polymer (e.g., polyurethane laminate), plastic, etc., that can readily be removed from the device prior to use. In addition, in embodiments where a further adhesive 204 is used in the devices, removable layer 302 suitably covers the adhesive 204 so as to prevent the device from sticking to a skin surface prior to a desired use, and also maintains the cleanliness of the adhesive.

Also provided herein are devices for treatment of skin or skin conditions, consisting essentially of a hydrocolloid dressing and the active agents vitamin A and dimethylethanolamine, each present at about 0.2% to about 0.7%, more suitably, each present at about 0.5%. Additional devices for treatment of skin or skin conditions are provided which consist essentially of a hydrocolloid dressing and the active agents vitamin A and zinc pyrrolidone, each present at about 0.2% to about 0.7%, more suitably, each present at about 0.5%. In embodiments, the amount of each active agent is present in the devices at 0.5%, with an error of less than 5% (i.e., 0.47% to 0.53% active agent).

In devices that consist essentially of the recited components, such devices contain the recited components and those that do not materially affect the basic and novel characteristics of the claimed devices. Components that do not materially affect the basic and novel characteristics of the claimed devices are those that do not limit to ability of the devices to deliver the active agent(s) to the skin surface, while also not reducing the absorption capability of the hydrocolloid dressing. Examples of components that would not materially affect the basic and novel characteristics of the claimed devices, and thus could be included in devices that consist essentially of the recited components, include various botanicals (e.g., aloe vera), scented oils, additional vitamins, etc.

Figure 4A:
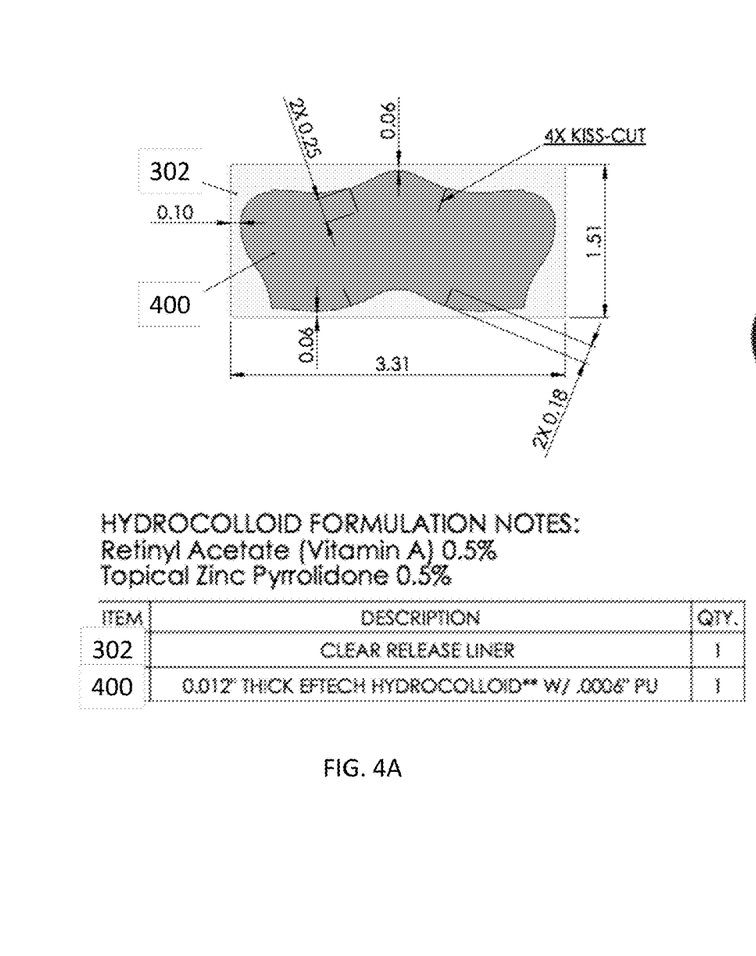
FIGS. 4A-4B shows a device and method of treating a skin condition as described in embodiments herein.
Figure 4B:
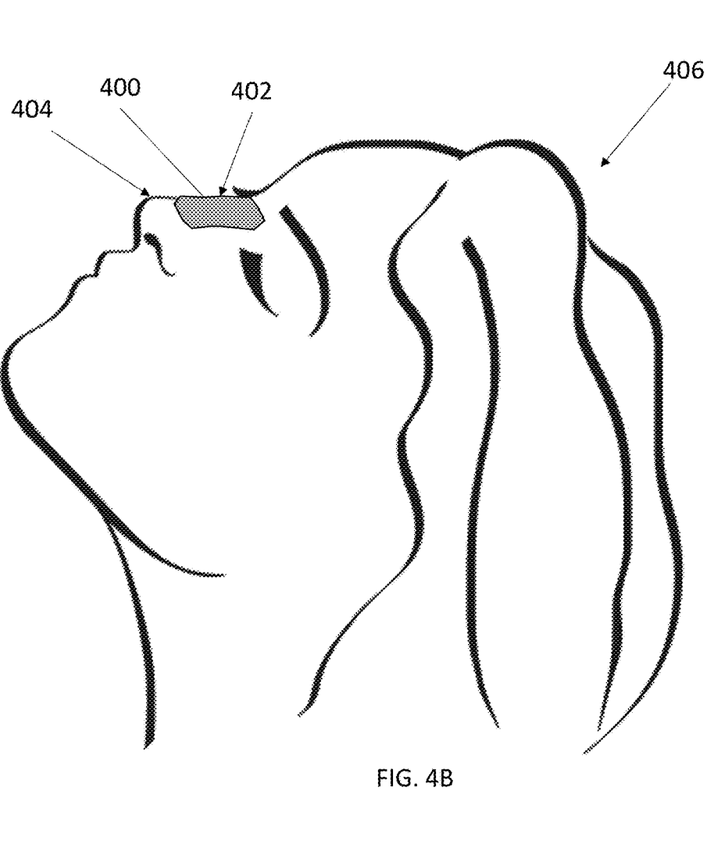

In further embodiments, devices that comprise or consist essentially of a hydrocolloid dressing and the active agents vitamin A and zinc pyrrolidone, each present at about 0.2% to about 0.7%, more suitably, each present at about 0.5%, are suitably used for treatment of blackheads on the skin. In embodiments, for example as shown in FIGS. 4A-4B, device 400 suitably has a shape (e.g., curved or contoured) that easily allows application of device 400 to a bridge 402 of a nose 404 of a patient 406, as shown in FIG. 4B. FIG. 4A shows exemplary measurements for device 400 to be applied to the bridge of the nose of a patient for treatment of a skin condition, such as blackheads. These dimensions are exemplary and should not be construed to limit the devices described herein.

It has been surprisingly found that in order to create device 400 that fits effectively and comfortably on the bridge of the nose of a patient, a thickness of the hydrocolloid dressing is suitably on the order of about 0.005 inches to about 0.015 inches, more suitably about 0.010 inches to about 0.013 inches, including about 0.008 inches, about 0.009 inches, about 0.010 inches, about 0.011 inches, about 0.012 inches, about 0.013 inches, about 0.014 inches or about 0.015 inches. Most suitably, the hydrocolloid dressing has a thickness of about 0.012 inches. As shown in FIG. 4B, having a hydrocolloid dressing with a thickness in the recited ranges, including about 0.012 inches, provides device 400 with a desired pliability and flexibility to be placed and fit over the bridge of the nose, allowing for adhesion to the nose and the device to function as described herein, while maintaining a comfortable fit for the patient, and also allowing delivery of the active agents associated with the device.

Figure 4C:
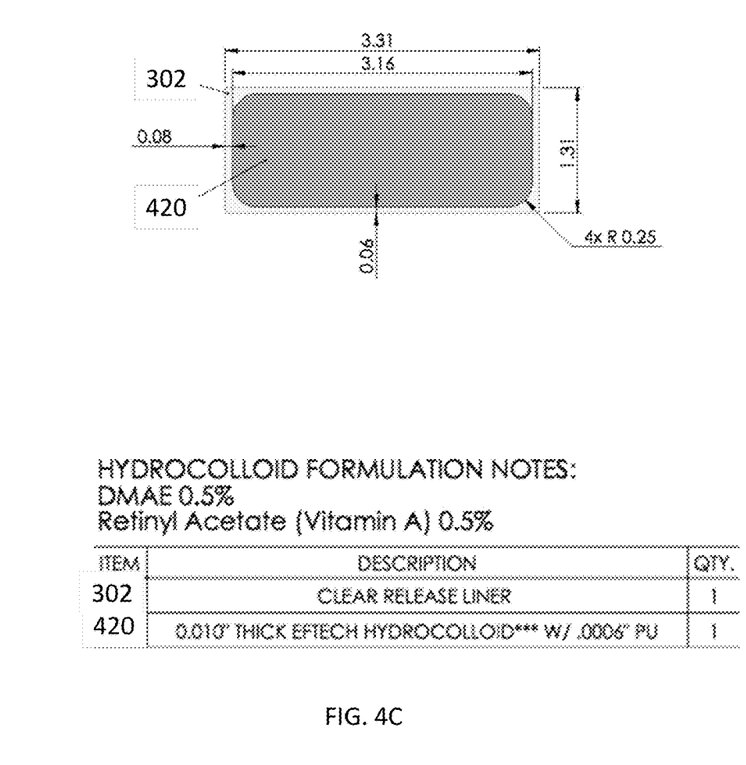
FIGS. 4C-4D shows a further device and additional method of treating a skin condition as described in embodiments herein.
Figure 4D:
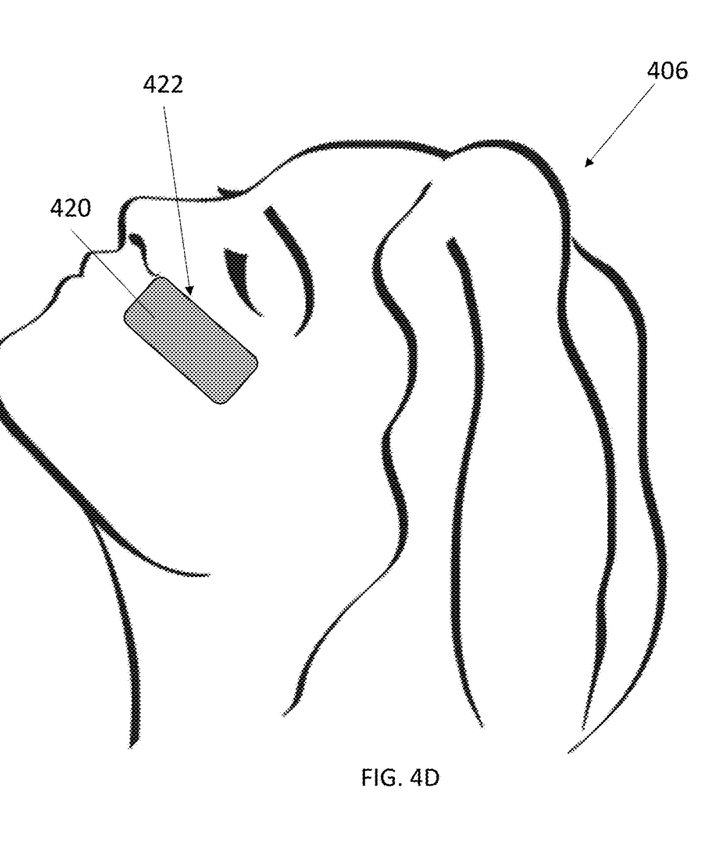

In further embodiments, devices that comprise or consist essentially of a hydrocolloid dressing and the active agents vitamin A and dimethylethanolamine, each present at about 0.2% to about 0.7%, more suitably, each present at about 0.5%, are suitably used for treatment of pores, including clogged pores, on the skin. In embodiments, for example as shown in FIGS. 4C-4D, device 420 suitably has a shape that easily allows application of device 420 to the surface of the skin, including for example a cheek 422 of patient 406, as shown in FIG. 4D. Additional areas of application for the device include other sections of the face, including the chin, forehead, nose, neck, as well as other areas of the body, including the trunk and back. FIG. 4C shows exemplary measurements for device 420 to be applied to the skin surface (e.g., cheek 422) of a patient for treatment of a skin condition, such as pores, including clogged pores. These dimensions are exemplary and should not be construed to limit the devices described herein.

It has been surprisingly found that in order to create device 420 that fits effectively and comfortably on the skin of a patient, including a curved skin surface such as the cheek or chin, a thickness of the hydrocolloid dressing is suitably on the order of about 0.005 inches to about 0.012 inches, more suitably about 0.008 inches to about 0.011 inches, or about 0.008 inches, about 0.009 inches, about 0.010 inches, or about 0.011 inches. Most suitably, the hydrocolloid dressing has a thickness of about 0.010 inches. As shown in FIG. 4D, having a hydrocolloid dressing with a thickness in the recited ranges, including about 0.010 inches, provides device 420 with a desired pliability and flexibility to be placed and fit over a curved skin surface such as the cheek or chin, allowing for adhesion to the skin surface and the device to function as described herein, while maintaining a comfortable fit for the patient, and also allowing delivery of the active agents associated with the device.

As described herein, devices 400 and 420 can suitably be provided adhered to removable layer 302, that provides a way to maintain the devices free of dirt and other contamination prior to application. Removable layer 302 (also called "clear release liner" in FIGS. 4A and 4C) is removed from the device (400 or 420), exposing the hydrocolloid dressing, which can then be applied to a skin surface. If a separate adhesive 204 is used, removal of removable layer 302 also exposes adhesive layer 204 so as to allow it to be applied to a skin surface. In other embodiments, removable layer need not be included, and devices 400 or 420 can simply be packaged together to form a system, or can be packaged together or separately, so as to maintain their cleanliness (including sterility if desired).

In additional embodiments, the devices 400 or 420 can be provided as multiple devices, each of which can be attached to the same removable layer 302. In such embodiments, removable layer 302 acts as a sheet from which devices 400 or 420 can be removed prior to use on a skin surface. Devices 400 or 420 can be packaged as multiple sheets, for example in box or other suitable container, prior to removal and use.

In embodiments of devices 400 and 420 described herein, can have any suitable or desired shape, including for example, square, circle, oval, rectangle, triangle, as well as irregular shapes, and also shapes that have specific configurations for use on different parts of the body, e.g., bridge of the nose, shoulders or back, chest, cheekbones, forehead, chin, etc.

Preparing devices 400 and 420 is suitably carried out by cutting larger sheets of hydrocolloid dressing into individual devices. For example, die cutting or kiss cutting can be used to prepare devices 400 and 420.

In a further embodiment, provided herein are methods of treating a skin condition, see FIG. 4B. In suitable embodiments, the methods comprise providing a device 400 as described herein, suitably having a thickness of about 0.005 inches to about 0.015 inches and active agents comprising vitamin A and zinc pyrrolidone associated with the hydrocolloid dressing. As described throughout, the active agent is present at an amount so as to not reduce the absorption capability of the hydrocolloid dressing. The methods further comprise maintaining the device on the skin surface for a period of at least 1 hour, thereby treating the skin condition. In the example shown in FIG. 4B, the skin condition is suitably a blackhead. A blackhead is known in the art as a clogged comedo, or hair follicle/pore, that is open, and can occur with or without acne. Oxidation generally causes the blackheads to appear black, and often appear one the bridge of the nose of a patient, and the nearby portions of the cheek.

In additional embodiments, provided herein are methods of treating a skin condition, see FIG. 4D. In suitable embodiments, the methods comprise providing a device 420 as described herein, suitably having a thickness of about 0.005 inches to about 0.012 inches and active agents comprising vitamin A and dimethylethanolamine associated with the hydrocolloid dressing. As described throughout, the active agent is present at an amount so as to not reduce the absorption capability of the hydrocolloid dressing. The methods further comprise maintaining the device on the skin surface for a period of at least 1 hour, thereby treating the skin condition. In the example shown in FIG. 4D, the skin condition is suitably a clogged or blocked pore, also known as a clogged comedo, or hair follicle. Clogged pores often occur on the face, in the areas of the cheek or chin, but can also appear on the forehead, etc., as well as in other areas such as the back or trunk.

Suitably, the skin surface is cleaned (e.g., using soap and/or water, or a suitable cleansing solution or agent) prior to applying the devices described herein.

The period that a device described herein is maintained on a skin surface can be as little as 10-15 minutes, but is suitably at least 1 hour, including maintaining the device on a skin surface for at least 6 hours (e.g., overnight) up to and including 12-24 hours.

Suitable skin surfaces onto which the devices can be applied include any surface where treatment is needed, including for example, the face, neck, back, shoulders, chest, buttocks, trunk, legs, etc. Suitably, the devices and methods described herein are useful in the treatment of skin conditions in mammals, and specifically humans.

In the methods of treatment described herein, the treatment is suitably repeated on a daily basis, though can be repeated on semi-daily (i.e., every 2, 3, 4, 5 days) etc., as desired. Suitably the treatment is repeated daily for at least 3 days, or until the skin condition is treated, or reduced, as desired by the user. The methods can be repeated for at least 3-30 days, e.g., about 7-14 days, or about 7-10 days.

In embodiments in which a removable layer 302 is included on an inner surface of the devices, the methods further comprise removing the removable layer prior to applying devices 400 or 420 to a skin surface.

In embodiments, such as shown in FIGS. 4A and 4C, removable layer 302 is removed from individual devices 400 or 420, prior to applying to a skin surface. In additional embodiments, removable layer 302 is removed from individual devices 400 or 420, leaving behind remaining devices on removable layer 302, suitably further comprising additional devices still attached to removable layer 302.

As described herein, applying the devices described herein to a skin surface to at least partially cover (suitably completely cover) one or more blackheads or one or more clogged pores, allows the hydrocolloid dressing to absorb impurities, including oil, pus, dirt, bacteria, etc., and also allow the active agents (e.g. vitamin A, dimethylethanolamine and/or zinc pyrrolidone) to absorb onto the surface the skin, begin to penetrate the skin, and have a treatment effect on the desired treatment area.

While in suitable embodiments a device can be removed and replaced immediately, in other embodiments, a period of time between removal and replacement is allowed to pass, suitably on the order of 15 minutes to several hours to days, suitably on the order of about 4-18 hours. For example, in embodiments, devices are removed from a skin surface during the day e.g., after waking in the morning, and then a new device reapplied at night, e.g., at bedtime.

The devices and methods described herein, while suitably useful for treatment of blackheads and clogged pores, can be useful for application to unclogged pores and for treatment of wrinkles, as well as other skin conditions, for example, for use in skin lightening or dark spot removal.

In further embodiments, provided herein are methods of preparing a device as described, the methods comprising providing a solution of an active agent(s) selected from vitamin A, dimethylethanolamine and zinc pyrrolidone, mixing the solution of the active agent(s) with a paste comprising a hydrocolloid, the mixing conducted at about 20-30° C., to form a mixture, and applying the mixture to a removable layer to generate the device. As described herein, it has been determined that the amount of active agent must be selected so as to be present at an amount as to not reduce the absorption capability of the hydrocolloid dressing.

Suitable active agents and components of the devices are described herein.

In further embodiments, the methods further comprise cutting the device into a plurality of separate devices, so as to aid in packaging and use by a patient.

Also provided herein are devices for treatment of skin conditions prepared by the processes described herein.

The components of the hydrocolloid composition are suitably provided as a powder. The power is combined with water to prepare a paste comprising the hydrocolloid composition.

The paste is then combined with a solution of active agent(s) having the desired final amount active agent (e.g., about 0.1% to about 10%) to create a mixture.

The resulting mixture is mixed using a stiff spatula to "swipe" the mass against the sides of the mixing container to avoid entrapment of air in the mix.

As active agents can react or gel chemically, temperature is an important factor in the setting time. The colder the temperature of the water the longer it takes to set; conversely, the higher the water temperature the faster it sets.

Suitably, a hydrocolloid composition (paste) and active agent(s) are mixed in a Banbury mixer at 30 RPM for about 30 minutes. The resulting active agent-containing hydrocolloid adhesive is then converted into a thickness of between about 0.005 inches up to about 0.015 inches, including the thicknesses described herein.

A hydrocolloid dressing sheet can be cut using a pressure point plaster die-cutting and packaging machine in order produce the hydrocolloid dressing into suitable sizes and shapes. For example, suitable sizes are about 0.5 cm to about 10 cm. In exemplary embodiments, each hydrocolloid dressing sheet can produce about 5-10 devices. These devices can be packaged into various containers or pouches prior to use or for storage.

The thickness of the different dressings is suitably determined using a Wallace thickness gauge, Model S.4 with 20.36 gram additive weight. In order to avoid localized compression of the dressing by the foot of the measuring gauge, a metal disc 20 mm in diameter of known thickness is placed upon the surface of the dressing and the combined thickness of the disc and dressing measured.

Exemplary Construction of Device as Described Herein

The following provides an exemplary construction of a device as described herein.

| Construction | | US Mil[1] | mm |
|---|---|---|---|
| Dressing: | Hydrocolloid | 20.0 | 0.51 |
| Laminate (carrier): | Matte Finish Polyurethane Film | 1.2 | 0.03 |
| Liner (removable layer): | 60# White Polycoated Kraft Paper | 4.5 | 0.11 |
| | Total Construction | 25.7 | 0.65 |

[1]A unit of length equal to one thousandth ($10^{-3}$) of an inch (0.0254 millimeter).

Exemplary Components of Hydrocolloid Dressing:
Benzene
Ethenyl-polymer with 2-methyl-1,3-butadiene
Hydrogenated
Ester with glycerol
Cellulose
Carboxymenthyl ether
Sodium salt
White mineral oil (petroleum)

An active agent as described herein is then dissolved in a suitable solvent and mixed with hydrocolloid to generate the devices. Suitable active agents and percentages are described herein.

The exemplary device provides the following features and benefits: medium initial tack aids in placement of product on skin; flexible and conformable; light in color and virtually transparent; no animal derived components; serializable by electron beam (EB) or Gamma radiation, as well as other means.

The devices were determined in compliance with ISO 10993, with regard to cytotoxicity, sensitization and irritation, and do not show the presence of mold or bacteria under standard, shelf-storage conditions.

The exemplary devices were found to have the following physical characteristics.

| Adhesive Properties | |
|---|---|
| Peel Adhesion Product 90° 12 in/min | Test Method: PTSC-101F |
| Substrate | US Oz/in |
| SS | 60-120 |
| Absorption Product in Saline Solution | 1" Diameter Sample |
| Substrate Product | % by weight/24 hours >300% |

The devices have been stored without degradation for a period of at least 24 months from date of manufacture at 72° F. (21° C.), 25% relative humidity, out of direct sunlight, in original packaging.

It will be readily apparent to one of ordinary skill in the relevant arts that other suitable modifications and adaptations to the methods and applications described herein can be made without departing from the scope of any of the embodiments. The following examples are included herewith for purposes of illustration only and are not intended to be limiting.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A device for treatment of skin, consisting of:
   a. a hydrocolloid having a thickness of about 0.005 inches to about 0.012 inches; and
   b. active agents consisting of vitamin A and dimethylethanolamine and optionally zinc pyrrolidone associated with the hydrocolloid,
   wherein the active agents are present at an amount so as to not reduce the absorption capability of the hydrocolloid.

2. The device of claim 1, wherein the active agents are present at an amount of about 0.1% to about 10%.

3. The device of claim 1, wherein the vitamin A and the dimethylethanolamine are each present at an amount of about 0.2% to about 0.7%.

4. The device of claim 3, wherein the vitamin A and the dimethylethanolamine are each present at an amount of about 0.5%.

5. The device of claim 1, wherein the hydrocolloid has a thickness of about 0.005 inches to about 0.011 inches.

6. The device of claim 1, wherein the active agents consist of vitamin A and dimethylethanolamine, each of about 0.5%.

7. A method of treating a skin condition, comprising:
   a. providing a device, the device consisting of:
      i. a hydrocolloid dressing having a thickness of about 0.005 inches to about 0.012 inches; and
      ii. active agents consisting of vitamin A and dimethylethanolamine and optionally zinc pyrrolidone associated with the hydrocolloid dressing,
   wherein the active agents are present at an amount so as to not reduce the absorption capability of the hydrocolloid dressing;
   b. applying the device to a skin surface; and
   c. maintaining the device on the skin surface for a period of at least 1 hour, thereby treating the skin condition.

8. The method of claim 7, wherein the skin condition is a clogged pore, and wherein the device is applied to a cheek, nose, forehead, or chin skin surface.

9. The method of claim 7, wherein the method of treatment is repeated daily for a period of at least 3 days.

* * * * *